United States Patent
Trott et al.

(10) Patent No.: US 10,488,831 B2
(45) Date of Patent: Nov. 26, 2019

(54) BIOPOTENTIAL WAKEUP WORD

(71) Applicant: BOSE CORPORATION, Framingham, MA (US)

(72) Inventors: Christian A. Trott, Charleston, SC (US); Christopher J. Mulhearn, Worcester, MA (US); Brian J. Hetherman, Westborough, MA (US); Michael J. Daley, Shrewsbury, MA (US)

(73) Assignee: BOSE CORPORATION, Framingham, MA (US)

( * ) Notice: Subject to any disclaimer, the term of this patent is extended or adjusted under 35 U.S.C. 154(b) by 136 days.

(21) Appl. No.: 15/819,973

(22) Filed: Nov. 21, 2017

(65) Prior Publication Data

US 2019/0155226 A1    May 23, 2019

(51) Int. Cl.
| | | |
|---|---|---|
| *G05B 13/02* | (2006.01) |
| *A61B 3/113* | (2006.01) |
| *A61B 5/0476* | (2006.01) |
| *A61B 5/0488* | (2006.01) |
| *A61B 5/0496* | (2006.01) |

(52) U.S. Cl.
CPC .......... *G05B 13/0265* (2013.01); *A61B 3/113* (2013.01); *A61B 5/0476* (2013.01); *A61B 5/0488* (2013.01); *A61B 5/0496* (2013.01)

(58) Field of Classification Search
CPC ...... G05B 13/0265; G05B 2219/23386; G05B 2219/24162; G05B 2219/32014; G05B 2219/35482; G05B 2219/39441; G05B 2219/40116; G05B 2219/405316; G05B 2219/45119; A61B 3/113; A61B 5/0476; A61B 5/0488; A61B 5/6803; G06F 3/013; G06F 3/015; G06F 3/017; G06F 3/167; H04R 1/1041

USPC ....................................... 340/10.33
See application file for complete search history.

(56) References Cited

U.S. PATENT DOCUMENTS

| | | | |
|---|---|---|---|
| 2008/0177197 A1* | 7/2008 | Lee ....................... | A61B 5/165 600/545 |
| 2013/0304479 A1 | 11/2013 | Teller et al. | |
| 2014/0214429 A1* | 7/2014 | Pantel .................... | G10L 21/16 704/275 |

(Continued)

FOREIGN PATENT DOCUMENTS

| | | |
|---|---|---|
| GB | 2396421 A | 6/2004 |
| WO | 2018226424 A1 | 12/2018 |

OTHER PUBLICATIONS

International Search Report and Written Opinion for International Application No. PCT/US2018/059427, dated Feb. 12, 2019, 18 Pages.

*Primary Examiner* — Edwin C Holloway, III
(74) *Attorney, Agent, or Firm* — Patterson + Sheridan, LLP

(57) ABSTRACT

Aspects of the present disclosure provide a product configured to obtain biological signals associated with a user. The biological signals may be used to trigger the product of an upcoming, separate command. The product may take action based on the received command. As described herein, the biological signals may comprise a change in electrical potential of a user, such as an EMG, EEG, or EOG signal. The separate command may be other biological signals, a voice command, or a gesture. The product may be configured to control itself and/or a device external to the product.

20 Claims, 2 Drawing Sheets

(56) References Cited

U.S. PATENT DOCUMENTS

| | | |
|---|---|---|
| 2015/0009124 A1 | 1/2015 | Antoniac |
| 2015/0215443 A1 | 7/2015 | Heo et al. |
| 2016/0284363 A1 | 9/2016 | Von Borstel et al. |
| 2016/0299570 A1* | 10/2016 | Davydov ................ G06F 1/163 |
| 2017/0112408 A1 | 4/2017 | Durand |
| 2017/0212590 A1* | 7/2017 | VanBlon ................ G06F 3/015 |
| 2018/0353128 A1* | 12/2018 | Farrell ................ A61B 5/6803 |

* cited by examiner

BIOPOTENTIAL WAKEUP WORD

BACKGROUND

Aspects of the present disclosure relate to using a voltage differential measured on a user's body as a wakeup word for an electronic product. More specifically, the voltage differential provides an indication to the product that a separate command may follow.

Currently, a special phrase, referred to as a "wakeup word," "wake word" or "keyword" is used to activate a speech recognition feature of an electronic device having a speech recognition system. As an example, the electronic device may listen continuously for the wakeup word. The electronic device may hear the wakeup word and process a following command.

SUMMARY

All examples and features mentioned herein can be combined in any technically possible manner.

According to an aspect, a product is provided. The product comprises a processor configured to detect a learned pattern of bio-signals associated with a user of the product, receive a separate command from the user after detecting the pattern of bio-signals, wherein the detected pattern of bio-signals triggers the processor to attempt to receive the separate command, and take action based on the received command.

In an aspect, the bio-signals comprise one of an electromyogram (EMG), electrooculogram (EOG), or electroencephalogram (EEG) signal. In an aspect, the bio-signals comprise a time-varying electrical potential associated with the user of the product.

In an aspect, the received command comprises at least a second bio-signal from the user. In an aspect, the received command comprises one of a gesture from the user or a voice command from the user. In an aspect, the received command comprises eye movement associated with the user.

In an aspect, the product further comprises a communication unit configured to communicate with a device external to the product and the processor configured to take the action is configured to control the device external to the product via the communication unit.

In an aspect, the processor configured to take the action is configured to adjust a volume of an output played by the product, enter a low power state at the product, or change an output of the product.

In an aspect, the processor configured to detect the learned pattern of bio-signals is configured to learn the pattern via training with the user.

According to an aspect, a product is provided comprising a first electrode, a second electrode, and a processor coupled to the first and second electrodes, wherein the processor is configured to: detect a learned pattern of signals collected via the first and second electrodes, in response to the detection, receive a separate command, wherein the detected pattern triggers the processor to attempt to receive the separate command, and take action to control one of the product or a device external to the product based on the command.

In an aspect, the signals comprise an electromyogram (EMG), electrooculogram (EOG), or electroencephalogram (EEG) associated with a user of the product. In an aspect, the command comprises one of an electromyogram (EMG), electrooculogram (EOG), or electroencephalogram (EEG) of a user of the product. In an aspect, the command comprises one of voice or movement associated with a user of the product.

In an aspect, the processor configured to take the action is configured to one of: adjust a volume of an output played by the product, enter a low power state at the product, or change an output of the product.

In an aspect, the processor configured to take the action is configured to change a mode of operation of the product.

According to an aspect, a method performed by a system is provided. The method comprises detecting a pattern of bio-signals associated with a user of the system, receiving a separate command from the user after detecting the bio-signals, wherein the detected pattern of bio-signals trigger attempting to receive the separate command, and taking action based on the received command.

In an aspect, the detecting is performed by a first device of the system, and the receiving and the taking action are performed by a second device of the system.

In an aspect, the bio-signals comprise one of an electromyogram (EMG), electrooculogram (EOG), or electroencephalogram (EEG) signal.

In an aspect, the separate command comprises a pattern of electrical potential associated with the user of the product.

In an aspect, the method comprises performing a machine-learned pattern recognition training with the user, wherein the detecting is based, at least in part, on the training.

DETAILED DESCRIPTION

Figure 1:
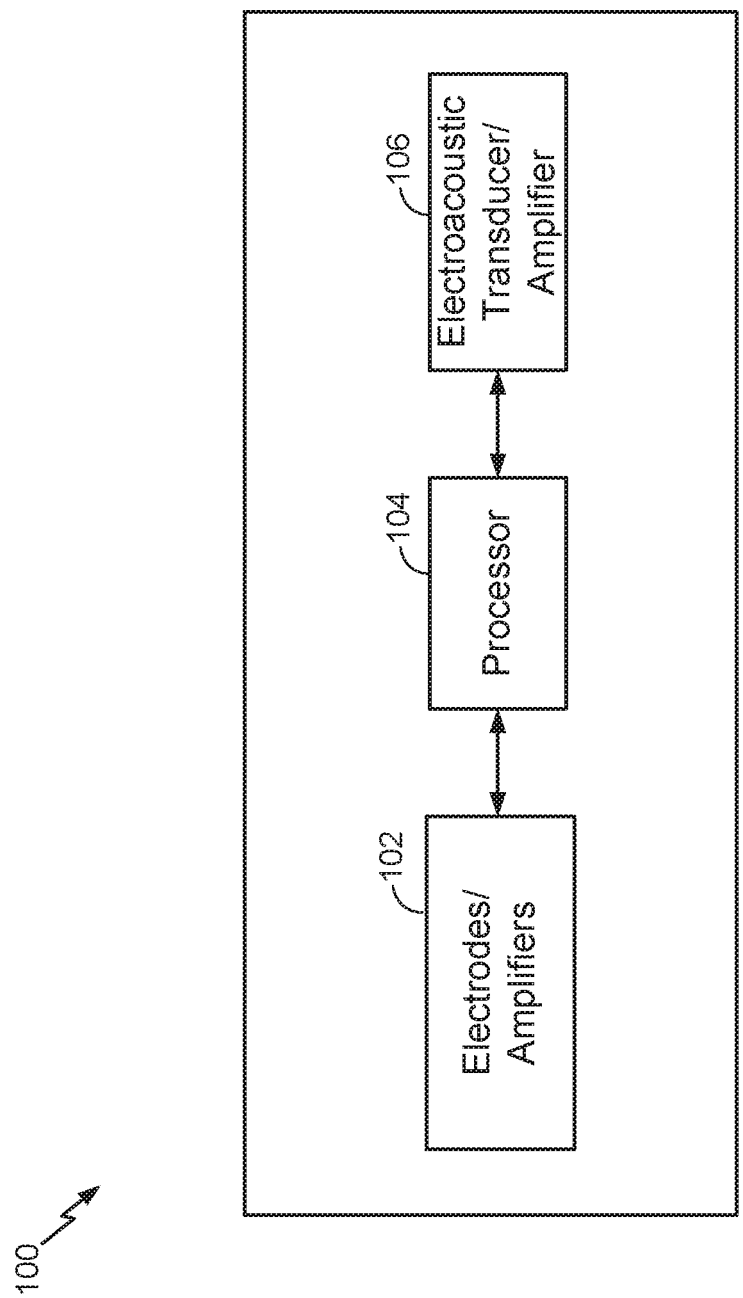
FIG. 1 is a block diagram of an example product.

Wearable electronic devices are being developed for use on or around the human head. Such devices may be configured to perform various functions, including collecting biometric data for health monitoring. According to an example, electrodes on a wearable device are used to measure electrophysiological signals ("bio-signals"). These signals can be used to identify patterns in, for example, a user's brain wave activity, muscle activity, or eye movements. Collected information may be used for a variety of purposes. Example uses of collected information include health monitoring, measuring states of sleep, determining an emotional state of a user, brain-computer interfaces, and hearing aid tuning. As the types of wearable technology increase, it will be beneficial to use measured bio-signals for other purposes.

Aspects of the present disclosure relate to a product configured to collect biologically-relevant information associated with a user of the product. As described herein, the product may be equipped with one or more capabilities to measure specific classes of bio-signals such as brain waves (electroencephalogram (EEG) signals), eye movement (electrooculogram (EOG) signals), or muscle activity (electromyogram (EMG) signals) associated with a user of the product. According to an example, the product may be an audio product.

The product may be configured to learn a pattern of bio-signals associated with a user. Upon detecting the learned pattern of bio-signals, the product may initiate an attempt to receive a separate subsequent command. Thus, the pattern of bio-signals functions as a wakeup word, triggering the product that a subsequent command may follow the detected wakeup word. As described herein, a bio-signal based wakeup word is not a "word" in the sense of spoken or written language. Rather, the wakeup word is an identifiable (for example, learned or trained) pattern of bio-signals that is used to trigger a subsequent command.

The use of a wakeup word based on bio-signals measured on a user's body helps to resolve ambiguity associated with traditional voice or gesture-based commands. In some cases, a bio-signal based wakeup word may be more robust at detecting the user intent than a voice or gesture based trigger. Additionally, a bio-signal-based wakeup word allows convenient, discreet control of a product. For example, a user may conveniently use a device, already in use for one purpose, to also control another device. A bio-signal-based wakeup word may be power-efficient in terms of battery consumption.

With the help of machine-based learning with the user, the product may be designed to robustly detect learned (for example, via training) bio-signals. Additionally, the bio-signal-based wakeup word allows a user to control a device based on thought, muscle activity, or eye movement, thereby allowing multimodal interactions with the product. According to an aspect, a user may activate the product to receive a command without speaking, making a gesture, or interacting with a manual user interface at the device.

FIG. 1 illustrates example components of a product 100 configured to receive bio-signals from a user of the product. The bio-signal-based wakeup word triggers the product to attempt to receive a separate command that may follow.

The product may include two or more electrodes/amplifiers 102, a processor 104, and, optionally, an electroacoustic transducer/amplifier 106.

According to one example, the product has two or more electrodes 102 placed within a user's ear. According to one example, the electrodes may each contact a same side of the user's body. For example, each of these electrodes contacts either a left side or right side of the user's body.

Generally, the electrodes are positioned on the product and are configured to collect bio-signals, in this case a time-varying voltage differential, associated with the user. The electrodes may be placed in a variety of places including on the ear lobe, the concha, or in the ear canal. For illustrative purposes only, according to other examples, electrodes may be placed over the user's auditory cortex, and one or more of: the user's occipital lobe or bridge of the user's nose. The locations for the multiple electrodes are provided for exemplary purposes only.

The processor 104 controls the general operation of the product 100. For example, the processor 104 performs processing and control for audio and/or data communication. In addition to the general operation, the processor 104 initiates processing one or more bio-signals received from electrodes 102 of the product 100 to detect the wakeup word and trigger an attempt to receive a separate command as described in more detail herein.

According to an example, the processor 104 may include software running on the processor for detecting a bio-signal-based wakeup word, for processing a received command after receiving the bio-signals, and for bio-signal pattern recognition and training. The bio-signal pattern recognition and training is configured to perform machine-learned pattern recognition training with a user of the product. Through training with the user, the product learns bio-signals associated with a specific thought, pattern of thoughts, movement, or pattern of movements that serve as a wakeup word. Over time, a user learns how to reliably emit the wakeup word. Through the training process, the number of false wakeup word triggers is reduced.

According to an example, the processor 104 includes a communication unit. When the product 100 operates in a system, the communication unit is configured to establish a communication link with one or more devices external to the product 100.

As an example, the communication unit may be controlled, at least in part, by the processor 104 to communicate to one or more other devices. As will be described in more detail herein, after receiving the bio-signal based wakeup word, the product 100 may trigger an external device to attempt to receive a subsequent command. For example, in response to the bio-signal based wakeup word, software executed by the processor 104 may trigger the communication unit to communicate with the external device to attempt to receive the subsequent command. The external device may receive the command and may take action in accordance with the received command. The action may relate to control of the external device or control of another device in the system.

The electroacoustic transducer/amplifier 106 may be also known as a driver or speaker. In some examples, more than one output transducer is used. The transducer converts electrical signals into sound.

The product may also include gesture and voice interfaces which are configured to receive and process a user's gesture or voice commands, respectively. The product may include a camera, microphone, (photoplethysmogram) PPG sensor, accelerometer, gyro, and/or other motion sensors. These interfaces and components may be coupled to the processor 104.

According to one example, the product 100 is a wireless headset.

Any or all of the components illustrated in or described with respect to FIG. 1 may be combined into multi-function components.

Figure 2:
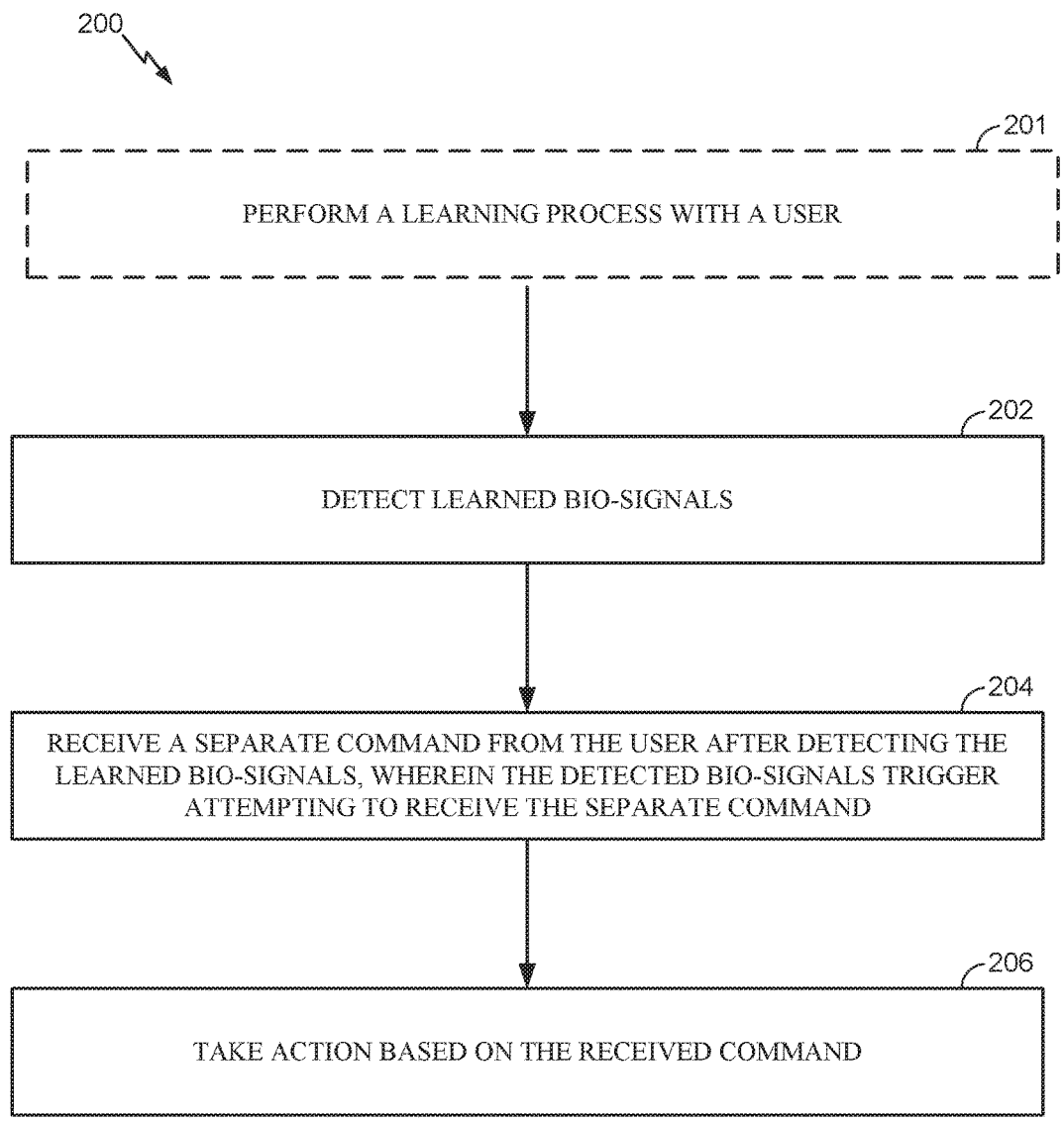
FIG. 2 is a flow diagram illustrating example steps performed by a product configured to receive a biopotential-based wakeup word.

FIG. 2 illustrates example operations 200 performed by a product, having one or more of the components illustrated in FIG. 1.

At 201, the product may perform a learning or training process with a user. As part of this process, the user learns how to emit biological (bio) signals that may be identifiable as a wakeup word by the product.

At 202, the product detects a learned pattern of bio-signals (a "wakeup word") associated with a user of the product. The bio-signals comprise time-varying electrical potentials associated with the user, as measured at the electrodes. According to an example, the bio-signals include at least one of an EMG, EOG, or EEG signal.

At 204, after detecting the wakeup word, the product attempts to receive the separate command. In certain scenarios, the received command is a voice command or gesture from the user. According to another example, the separate command is based on other learned bio-signals from the user, such as eye movement, muscle movement, or brain activity. The bio-signals may include any time varying voltage differential measured on the user's body, such as an EMG, EOG, or EEG signal.

At 206, the product takes action based on the received command. The product may control a device external to the product or control the product itself. As an example, the product may communicate with a home system, camera, loud speaker system, cell phone, telephone or another electronic device external to the product. Based on the separate command, received after the wakeup word, the product may control the other electronic device, or it may trigger the other device to itself receive the separate command directly from the user.

For example, the product may modify a power preference by turning the electronic device or the product on, off, or causing the product or device to enter a low-power state. The product may control the function or mode of the electronic device or the product. The mode may activate secondary features or functions on the product or device, similar to using the "Alt" key on a computer keyboard. According to an aspect, the product may change the volume or output (change a song or type of music) of the electronic device or the product.

As described with respect to FIG. 2, a same product may detect a wakeup word associated with a user of the system which triggers the product to receive a separate, subsequent command. According to aspects, a system including two or more products or devices may perform the methods described herein. The products or devices may communicate with each other and may each include one or more of the components illustrated or described with respect to FIG. 1.

According to an example, a system may detect a wakeup word associated with a user of the system. The system may receive a separate command from the user after detecting the wakeup word. The wakeup word triggers the system to attempt to receive the separate command. The system may take action based on the received command. The multiple devices in the system may perform machine-learned pattern recognition training with the user. Based on the training, certain devices may be configured to detect learned bio-signals and/or the separate, subsequent command.

A single product may detect the wakeup word, receive a separate command after receiving the wakeup word, and take action based on the received command. The device may take action to control itself or an external device.

According to another example, a first device or product in the system detects the wakeup word. The wakeup word triggers another device or product in the system, such as a second device, to attempt to receive a separate, subsequent command. If the second device receives the subsequent command it takes action in accordance with the received command. The second device may take action to control itself or another device in the system. According to an example, a first product or device may receive an EEG wakeup word, which triggers a second product or device to attempt to receive a subsequent command, such as a voice command. The second product or device takes action in accordance with the received command.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but is to be accorded the widest scope consistent with the principles and novel features disclosed herein.

The invention claimed is:

1. A system comprising:
  an audio output device and a second product,
  wherein the audio output device comprises a processor configured to:
    detect a learned pattern of bio-signals associated with a user of the audio output device; and
  wherein the second product comprises a processor configured to:
    receive a separate command from the user after the audio output device detects the learned pattern of bio-signals, wherein the detection of the learned pattern of bio-signals by the audio output device triggers the processor of the second product in the system to attempt to receive the separate command; and
    take action based on the received command.

2. The system of claim 1, wherein the bio-signals comprise one of an electromyogram (EMG), electrooculogram (EOG), or electroencephalogram (EEG) signal.

3. The system of claim 1, wherein the bio-signals comprise a time-varying electrical potential associated with the user of the system.

4. The system of claim 1, wherein the received command comprises at least a second bio-signal from the user.

5. The system of claim 1, wherein the received command comprises one of a gesture from the user or a voice command from the user.

6. The system of claim 1, wherein the received command comprises eye movement associated with the user.

7. The system of claim 1, wherein the second product further comprises:
  a communication unit configured to communicate with the device external to the second product.

8. The system of claim 1, wherein the processor of the second product is configured to take the action by adjusting a volume of an output played by the second product, enter a low power state at the second product, or change an output of the second product.

9. The system of claim 1, wherein the processor of the audio output device is configured to detect the learned pattern of bio-signals via training with the user.

10. A system product comprising:
  a first product and a second product,
  wherein the first product comprises:
    a first electrode;
    a second electrode; and
    a processor coupled to the first and second electrodes, wherein the processor is configured to: detect a learned pattern of signals collected via the first and second electrodes; and
  wherein the second product comprises a processor configured to:
    in response to the detection, receive a separate command, wherein the
    detected pattern triggers the processor of the second product to attempt to receive the separate command; and
    take action to control one of the second product or a device external to the second product based on the command.

11. The system of claim 10, wherein the signals comprise an electromyogram (EMG), electrooculogram (EOG), or electroencephalogram (EEG) associated with a user of the system.

12. The system of claim 10, wherein the command comprises one of an electromyogram (EMG), electrooculogram (EOG), or electroencephalogram (EEG) of a user of the system.

13. The system of claim 10, wherein the command comprises one of voice or movement associated with a user of the system.

14. The of claim 10, wherein the processor of the second product is configured to take the action by one of: adjusting a volume of an output played by the second product or the device external to the second product, entering a low power state at the second product or the device external to the second product, or changing an output of the second product or the device external to the second product.

15. The system of claim 10, wherein the processor of the second product is configured to take the action by changing a mode of operation of the second product or the device external to the second product.

16. A method performed by a system, comprising:
    detecting, by a wearable audio output device, a pattern of bio-signals associated with a user of the system;
    receiving, by a second device in the system, a separate command from the user after the wearable audio output device detects the pattern of bio-signals, wherein the detected pattern of bio-signals triggers the second device to attempt to receive the separate command; and
    taking action, by the second device in the system, based on the received command.

17. The method of claim 16, wherein:
    taking the action comprises one of controlling the second device or another device in the system.

18. The method of claim 16, wherein the bio-signals comprise one of an electromyogram (EMG), electrooculogram (EOG), or electroencephalogram (EEG) signal.

19. The method of claim 16, wherein the separate command comprises a pattern of electrical potential associated with the user of the product.

20. The method of claim 16, further comprising:
    performing by the wearable audio output device, a machine-learned pattern recognition training with the user,
    wherein the detecting is based, at least in part, on the training.

* * * * *